United States Patent
Ueta et al.

(10) Patent No.: US 10,478,601 B2
(45) Date of Patent: Nov. 19, 2019

(54) APPLICATOR

(75) Inventors: Masahiro Ueta, Bunkyo-ku (JP); Ryouhei Sakaguchi, Ichinomiya (JP); Ryouji Takei, Souka (JP); Katsumi Sasama, Sumida-ku (JP); Katsuya Taguchi, Chiyoda-ku (JP)

(73) Assignee: KAKEN PHARMACEUTICAL CO., LTD., Tokyo (JP)

( * ) Notice: Subject to any disclaimer, the term of this patent is extended or adjusted under 35 U.S.C. 154(b) by 1025 days.

(21) Appl. No.: 14/130,822

(22) PCT Filed: Jul. 4, 2012

(86) PCT No.: PCT/JP2012/004352
§ 371 (c)(1),
(2), (4) Date: Apr. 10, 2014

(87) PCT Pub. No.: WO2013/005434
PCT Pub. Date: Jan. 10, 2013

(65) Prior Publication Data
US 2014/0257208 A1 Sep. 11, 2014

(30) Foreign Application Priority Data
Jul. 5, 2011 (JP) ................. 2011-149605

(51) Int. Cl.
*A61M 35/00* (2006.01)
*A46B 11/00* (2006.01)
*A46B 11/06* (2006.01)

(52) U.S. Cl.
CPC ......... *A61M 35/003* (2013.01); *A46B 11/001* (2013.01); *A46B 11/0082* (2013.01)

(58) Field of Classification Search
CPC . A61M 35/003; A46B 11/001; A46B 11/0082
See application file for complete search history.

(56) References Cited

U.S. PATENT DOCUMENTS

| | | | |
|---|---|---|---|
| 2,333,070 A | 10/1943 | Hoey et al. | |
| 3,864,183 A | * 2/1975 | Hori | B43K 1/12 |
| | | | 156/180 |

(Continued)

FOREIGN PATENT DOCUMENTS

| | | |
|---|---|---|
| EP | 0 475 425 A1 | 3/1992 |
| GB | 2 227 650 A | 8/1990 |

(Continued)

OTHER PUBLICATIONS

European Search Report dated Mar. 12, 2015 issued in application No. 12807991.0.

(Continued)

*Primary Examiner* — Benjamin J Klein
*Assistant Examiner* — Sara A Sass
(74) *Attorney, Agent, or Firm* — Sughrue Mion, PLLC

(57) ABSTRACT

To provide a solution applicator with which irritation on an affected part of a patient may be reduced even when a solution is used.

According to the present invention, an applicator comprises a solution container which comprises an opening, and a columnar brush member formed by bundling synthetic fibers in a columnar shape. The columnar brush member is disposed at the opening of the solution container, a tip portion of the columnar brush member at an outside of the solution container has a fan shape expanding in a perpendicular lateral direction against a pillar axial lengthwise direction, and a thickness of the fan-shaped tip portion of the columnar brush member decreases in a perpendicular lengthwise direction against the pillar axial lengthwise direction toward the tip portion of the columnar brush member. The solution applicator of the present invention has the fan-shaped tip (Continued)

portion so that irritation on an affected part may be decreased and a liquid tinea unguium medicine may be applied to the affected part.

16 Claims, 23 Drawing Sheets

(56) References Cited

U.S. PATENT DOCUMENTS

| | | | | |
|---|---|---|---|---|
| 3,998,982 | A * | 12/1976 | Mauleon | B43K 1/12 |
| | | | | 156/180 |
| 4,310,259 | A * | 1/1982 | Ito | B29C 48/30 |
| | | | | 401/265 |
| 6,073,634 | A * | 6/2000 | Gueret | A45D 40/22 |
| | | | | 132/218 |
| 7,044,937 | B1 | 5/2006 | Kirwan et al. | |
| 7,607,848 | B1 * | 10/2009 | Ahmed | B43K 1/12 |
| | | | | 401/34 |
| 2003/0075201 | A1 | 4/2003 | Saito | |
| 2004/0018037 | A1 * | 1/2004 | Gueret | A46B 9/021 |
| | | | | 401/126 |
| 2004/0047676 | A1 | 3/2004 | Dumler | |
| 2008/0195040 | A1 | 8/2008 | Clark et al. | |
| 2009/0279937 | A1 * | 11/2009 | Peck | A45D 40/0087 |
| | | | | 401/128 |

FOREIGN PATENT DOCUMENTS

| | | |
|---|---|---|
| JP | 02-091681 U | 7/1990 |
| JP | 2003-189929 A | 7/2003 |
| JP | 2008169163 A | 7/2008 |
| WO | 2008/092068 A2 | 7/2008 |

OTHER PUBLICATIONS

Chinese Office Action dated Jun. 3, 2015 issued in corresponding Application No. 201280033495.7.
International Search Report for PCT/JP2012/004352 dated Aug. 7, 2012.
Communication dated Aug. 18, 2015, issued by the Japan Patent Office in corresponding Japanese Application No. 2011-149605.
Communication dated Jan. 12, 2016, issued by the Australian Patent Office in counterpart Australian Application No. 2012279752.
English translation of communication dated Mar. 22, 2016, from the Japanese Patent Office in counterpart application No. 2011-149605.
Communication dated Mar. 7, 2016 from the Mexican Industrial Property Office in counterpart application No. MX/a/2013/014110.
Communication dated Apr. 5, 2016 from the Russian Patent Office in counterpart application No. 2014103817/14.
Communication dated Oct. 7, 2015, issued by the Mexican Institute of Industrial Property in corresponding Mexican Application No. MX/a/2013/014110.
Communication dated Oct. 10, 2016 from the Mexican Patent Office in counterpart Application No. MX/a/2013/014110.
Communication dated Apr. 18, 2018, from the Canadian Intellectual Property Office in corresponding Application No. 2,839,113.
Communication dated Jun. 18, 2018, from the European Patent Office in counterpart European Application No. 12 807 991.0.
Communication dated Jul. 31, 2018, issued by the Korean Intellectual Property Office in corresponding Korean Application No. 10-2014-7000026.
Canadian Office Action dated Dec. 10, 2018 for Application No. 2,839,113; 4 pages.

* cited by examiner

APPLICATOR

TECHNICAL FIELD

The present invention relates to an applicator for applying an athlete's foot medicine and so on to a body surface, particularly to an applicator for applying a liquid tinea unguium medicine to an affected part of a patient.

BACKGROUND ART

A toenail infected with *Trichophyton* can exhibit a symptom called tinea unguium. In fact, tinea unguium causes daily life problems attributed to a terminal and progressive symptom of athlete's foot with e.g. a brittle nail which will break off and come away.

Drugs for treating tinea unguium have conventionally been developed and they can readily be available at a drugstore. By applying the drugs to an affected part of a patient, tinea unguium symptoms can be eased in daily life.

Nevertheless, when the drugs are applied to a skin from which a nail has come away or applied between nails, some patients actually exhibit unbearable pain according to the degree of progression of a tinea unguium symptom.

When a commercially available creamy drug is used for treatment, it is necessary to rub the creamy drug on an affected part with fingers.

However, direct irritation on the affected part with fingers fails to ease pain thereon.

When a spray drug is used on an affected part, injection pressure of the spray drug irritates the affected part, thereby making it difficult to ease pain thereon.

Meanwhile, a drug contained in a one-push type container is also commercially available. Specifically, by pushing the tip of the drug container against an affected part, a valve mechanism provided inside the drug container is operated to discharge a drug inside the drug container.

However, it is necessary to push the tip portion against the affected part by pressurizing the drug contained in the one-push type container, thereby making it difficult to ease pain on the affected part.

While it is possible to apply a solution to an affected part by using a brush, a series of operations, unscrewing a cap of a solution container, putting a brush into a solution and applying a solution to the affected part with the brush, are required when a brush is used. This method is unfortunately prone to practical problems.

In view of the above problems, a drug applicator is being developed in order to reduce work for applying a drug to an affected part (Patent Document 1). The drug applicator comprises a coating part having a high water retentivity which is disposed at an opening of a drug container.

However, since the coating part of the drug applicator has a hemispheric shape, the drug applicator fails to apply a drug between nails.

In the meantime, a drug applicator having a brush is commercially available.

Nevertheless, conventional drug applicators can cause liquid dripping when a brush of the drug applicator is faced downward.

In this case, the solution moves to the tip of the brush to generate liquid droplets. To prevent the liquid droplets from falling on a non-affected part, a patient needs to push the tip of the brush against the affected part.

Since the tip of the brush is directly pushed against the affected part to irritate the same, a conventional drug applicator fails to ease pain on the affected part.

PRIOR ART DOCUMENT

Patent Document

Patent Document 1: Japanese Unexamined Patent Publication No. 2000-116793

SUMMARY OF THE INVENTION

Problems to be Solved by the Invention

The objective of the present invention is to provide an applicator capable of reducing irritation on an affected part of a patient, even when a solution is used.

Means for Solving the Problems

Inventors of the present invention carried out extended research, in order to find out that the objective of the present invention corresponds to that of an applicator comprising a solution container and a columnar brush member, wherein the columnar brush member formed by bundling synthetic fibers in a columnar shape is disposed at the opening of the solution container, a tip portion of the columnar brush member has a fan shape extending in a perpendicular lateral direction against a pillar axial lengthwise direction, and a thickness of the tip portion of the columnar brush member decreases in a perpendicular lengthwise direction against the pillar axial lengthwise direction toward the tip portion of the columnar brush member to complete the present invention.

Specifically, the present invention provides

[1] an applicator, comprising a solution container having an opening and a columnar brush member formed by bundling synthetic fibers in a columnar shape, wherein
the columnar brush member is disposed at the opening of the solution container,
a tip portion of the columnar brush member outside the solution container has a fan shape extending in a perpendicular lateral direction against a pillar axial lengthwise direction, and a thickness of the fan-shaped tip portion of the columnar brush member decreases in a perpendicular lengthwise direction against the pillar axial lengthwise direction toward the tip portion of the columnar brush member.

The present invention includes the applicator described in the above item [1], wherein
[2] the maximum width of the fan-shaped tip portion of the columnar brush member is 1.1 to 2.0 times the maximum size of a columnar portion of the columnar brush member, with a cross section by a plane horizontal to the pillar axial lengthwise direction of the columnar brush member as a standard.

The present invention includes the applicator described in the above item [1] or [2], wherein
[3] the columnar brush member is formed by bundling synthetic fibers 7 to 50 μm in diameter so that the density ranges from 0.15 to 0.65.

The present invention includes the applicator described in any of the above items [1] to [3], wherein
[4] synthetic fibers used for the columnar brush member are at least one selected from the group consisting of polyester fibers, nylon fibers and acrylic fibers.

The present invention includes the applicator described in any of the above items [1] to [4], wherein
[5] the columnar brush member is obtained by grinding a plurality of synthetic fibers bundled impregnated with an adhesive and formed in a columnar shape,
the adhesive is contained on the outer periphery of the synthetic fibers bundled in large quantities,
a tip portion of the synthetic fibers bundled is ground to be unraveled over the entire outer periphery of at least one end of the synthetic fibers bundled, and
synthetic fibers of part or all of the tip portion of the synthetic fibers bundled move by contact stress in use.
The present invention includes the applicator described in any of the above items [1] to [5], wherein
[6] a bottomed tubular holder having a tubular body and a bottom portion is provided between the solution container and the columnar brush member,
the bottomed tubular holder is inserted into the opening of the solution container,
the bottom portion of the bottomed tubular holder has at least one pore, and
the columnar brush member is inserted into the inside of the tubular body of the bottomed tubular holder.
The present invention includes the applicator described in the above item [6], wherein
[7] the bottomed tubular holder comprises a supporting member inside the same, and
the supporting member supports the columnar brush member inserted into the inside of the bottomed tubular holder.
The present invention includes the applicator described in the above item [6] or [7], wherein
[8] a space is provided between an end face of the columnar brush member closely inserted into the inside of the bottomed tubular holder and the bottom portion of the bottomed tubular holder.
The present invention includes the applicator described in any of the above items [1] to [8], wherein
[9] the applicator comprises a lid member, wherein the lid member is sealed and fixed to the solution container.
The present invention includes the applicator described in any of the above items [1] to [9], wherein
[10] a volatile solution is contained in the solution container.

Advantageous Effect of the Invention

The tip portion of the columnar brush member used in the present invention outside the solution container has a fan shape, and a thickness of the fan-shaped tip portion of the columnar brush member decreases toward the tip of the columnar brush member.
Accordingly, a solution can applied between the nail and the skin by using the fan-shaped tip portion of the columnar brush member and a solution can be applied on an affected part by using a fan-shaped angle portion of the columnar brush member, and the applicator of the present invention can readily be used. Therefore, the applicator of the present invention is useful particularly when a liquid tinea unguium medicine is applied on an affected part.
Moreover, since synthetic fibers used for the columnar brush member are small in diameter, the tip portion of the columnar brush member is significantly soft, resulting in less irritation on an affected part of a patient. Thus, pain on the affected part of a patient can be eased when a solution is applied.

BEST MODE FOR CARRYING OUT THE INVENTION

The present invention will be described in more detail with reference to the following drawings and Examples. The present invention is not restricted to the following Examples.

Example 1

Figure 1:
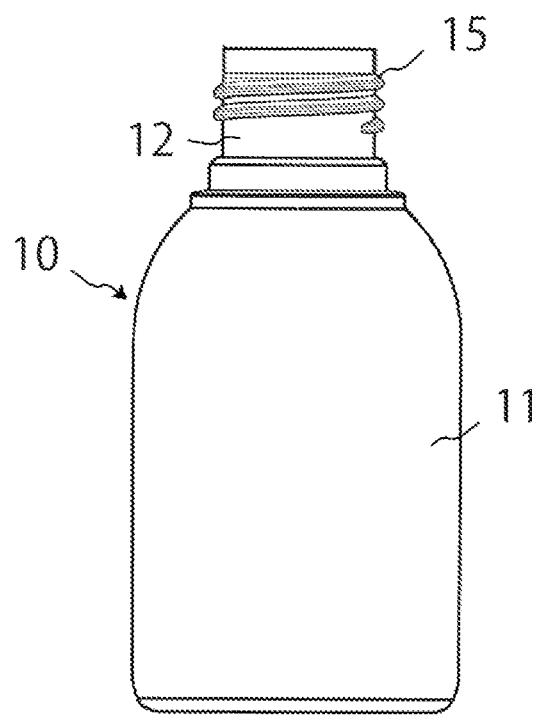
FIG. 1 is a schematic front view for describing a solution container used in Example 1.
Figure 2:
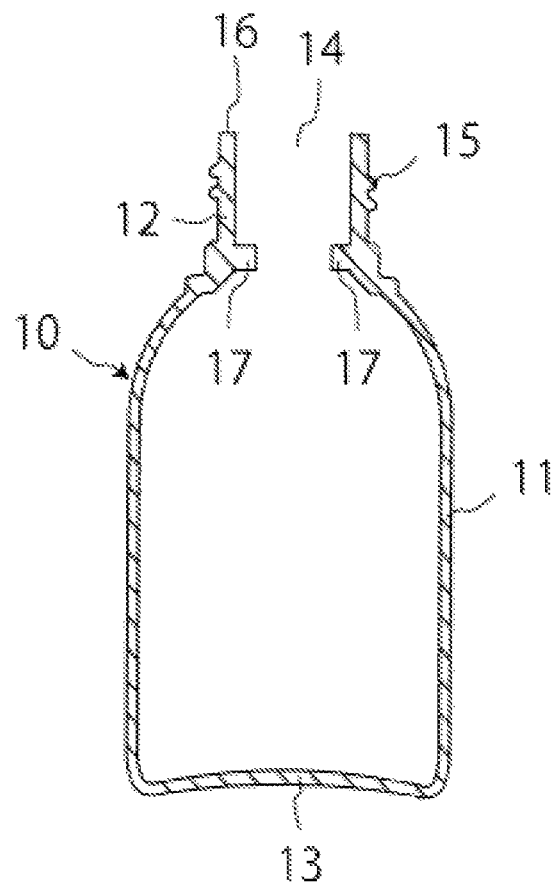
FIG. 2 is a schematic sectional view of a solution container used in Example 1.
Figure 3:
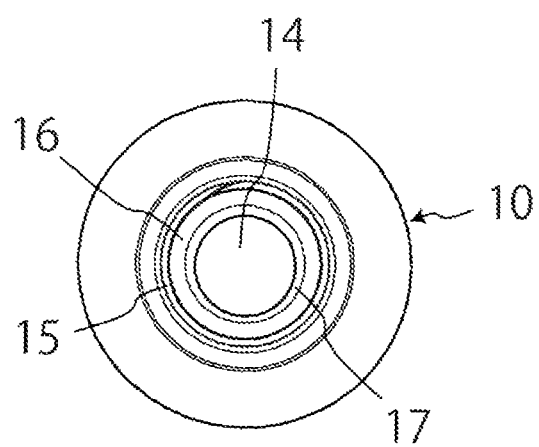
FIG. 3 is a schematic plan view illustrating a solution container used in Example 1 viewed from above.

An applicator 100 according to Example 1 comprises at least a solution container and a columnar brush member. At first, a solution container used in Example 1 will be described.
FIG. 1 is a schematic front view for describing a solution container used in Example 1, FIG. 2 is a schematic sectional view of a solution container illustrated in FIG. 1, and FIG. 3 is a schematic plan view illustrating a solution container illustrated in FIG. 1 viewed from above.
A solution container 10 used in the present invention comprises a solution container body 11 and a solution container neck portion 12. The shape of the solution container body 11 is not particularly restricted if it can retain a solution inside the same.

A bottom face of the solution container body 11 preferably has a shape that can stably contact with a horizontal plane so that the solution container 10 cannot readily fall down when a solution is placed inside the solution container 10 and the solution container 10 is put on a plane such as a desk.

The solution container body 11 has an approximately columnar shape, and an upper portion thereof is continuously formed with the solution container neck portion 12 via a curved surface.

A bottom portion 13 of the solution container body 11 forms an approximately sphere toward inside the solution container body 11.

By forming the bottom portion 13 of the solution container body 11 in an the approximately sphere toward inside the solution container body 11, it is possible to prevent the bottom portion 13 of the solution container body 11 from externally expanding even when the internal pressure of the solution container 10 increases due to evaporation of volatile components of a solution.

Consequently, the bottom portion 13 of the solution container body 11 externally expands to make the solution container 10 unstable, thereby preventing the solution container 10 placed on e.g. a desk from tumbling down.

The solution container 10 comprises the solution container neck portion 12.

An end portion of the solution container neck portion 12 is provided with a circular opening 14. A solution can be injected inside the solution container 10 via the circular opening 14.

An outer surface of the solution container neck portion 12 is provided with a screw thread 15. The inside of the solution container 10 can be sealed with a later-described lid member by using the screw thread 15.

An inner surface of the solution container neck portion 12 is provided with a protruding portion 17 for supporting a later-described columnar brush member.

The material of the solution container 10 used in Example 1 is not particularly restricted if it can retain a solution inside the same, but illustrative example thereof includes: a polyolefin such as a polyethylene and a polypropylene; an organic material such as an aromatic polyester including a polyethylene terephthalate and a polybutylene terephthalate; and an inorganic material such as glass and ceramics.

It is preferable that the material be an organic material because it needs to be light-weight and impact-resistant.

The material can be used alone or in combination with one or more types thereof.

Next, a columnar brush member used in Example 1 will be described.

Figure 4:
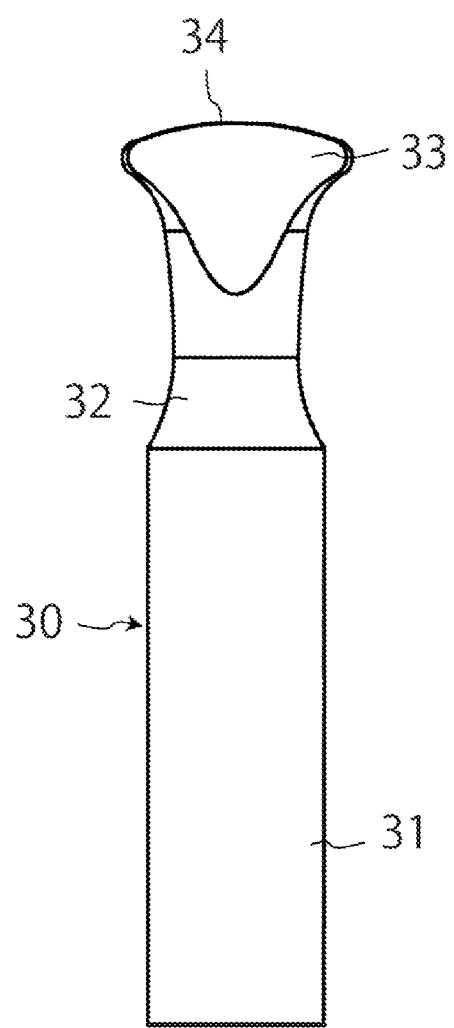
FIG. 4 is a schematic front view for describing a columnar brush member used in Example 1.
Figure 5:
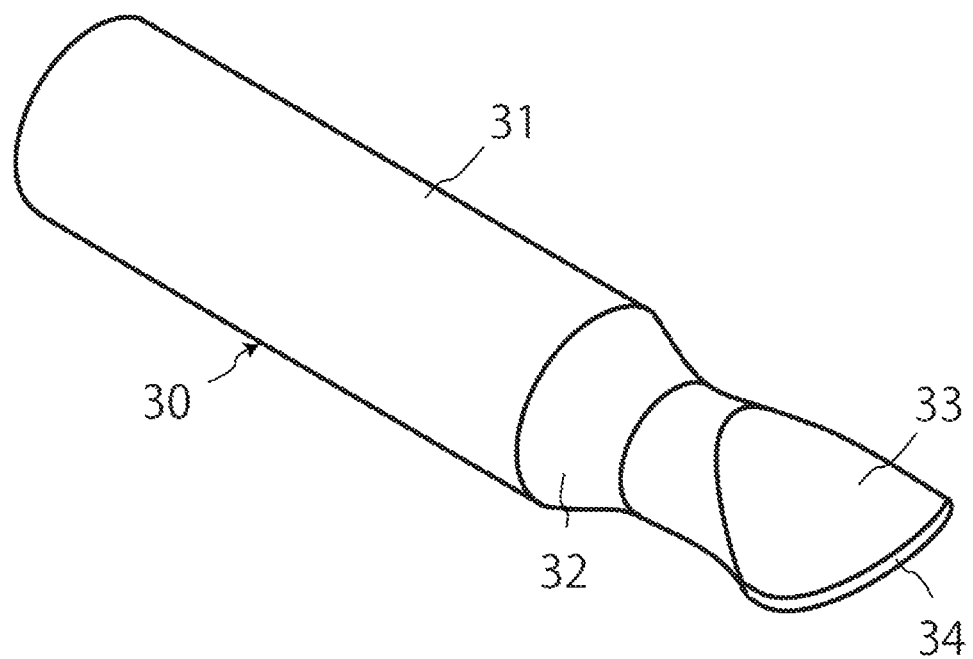
FIG. 5 is a schematic perspective view for describing a columnar brush member used in Example 1.
Figure 6:
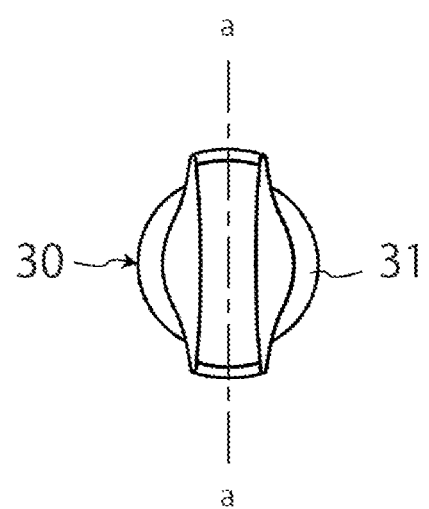
FIG. 6 is a schematic plan view illustrating a columnar brush member observed from a tip direction.

FIG. 4 is a schematic front view for describing the columnar brush member used in Example 1, FIG. 5 is a schematic perspective view for describing the columnar brush member used in Example 1, and FIG. 6 is a schematic plan view illustrating a columnar brush member observed from a tip direction illustrated in FIG. 4.

A columnar brush member 30 used in Example 1 is obtained by bundling a plurality of synthetic fibers composed of polyester fibers 18 μm in diameter with a fineness of 3.3 dtex to be formed into a columnar shape with a density of 0.42 (porosity: 58%).

The density in the present invention means the rate of synthetic fibers per sectional area to an adhesive gluing the same, with a cross section cut perpendicular to a pillar axial lengthwise direction of the columnar brush member 30 as a standard.

The volume of the columnar brush member 30 used in this Example is 490=$^3$. The volume of the columnar brush member 30 is preferably 400 to 600=$^3$.

The volume of the columnar brush member 30 depends on the capacity of a solution that permeates by capillarity to be retained by the columnar brush member 30 and the viscosity of a solution. When the viscosity of a solution used in the present invention is low, the volume of the columnar brush member 30 is preferably increased. Conversely, when the viscosity of a solution used in the present invention is high, the volume of the columnar brush member 30 is preferably decreased.

If the volume of the columnar brush member 30 is too small, the delivering property of the solution worsens and if the volume of the columnar brush member 30 is too large, liquid dripping can readily be observed.

The columnar brush member 30 comprises a columnar brush member body 31, a columnar brush member neck portion 32 and a columnar brush member tip portion 33.

Outer surfaces of the columnar brush member body 31 and the columnar brush member neck portion 32 are solidified with an adhesive, and synthetic fibers composed of fine polyester fibers contained inside the columnar brush member 30 are integrated.

Since a gap for supplying a solution is provided between the synthetic fibers inside the columnar brush member body 31 and the columnar brush member neck portion 32, the solution exudes from other ends of the synthetic fibers by capillarity when an end face of the columnar brush member body 31 is put in a solution.

A method for forming the columnar brush member body 31 is described as follows.

First, a plurality of polyester fibers are bundled and arranged in a pillar axial lengthwise direction and fed into a heated mold to obtain columnar polyester synthetic fibers bundled having a predetermined diameter.

The columnar synthetic fibers bundled are carefully infiltrated into an adhesive diluted with a solvent so that its shape is maintained. After drying the solvent and hardening the adhesive, the columnar synthetic fibers bundled are cut into a predetermined length to obtain the columnar brush member body 31.

Illustrative example of the resin for gluing the synthetic fibers bundled includes: a thermosetting resin such as an unsaturated polyester, a urea formaldehyde, a phenol, an epoxy, a melamine and a polyurethane; and a thermoplastic resin such as a polyvinyl acetate, a polyolefin and a low-melting polyester, and preferably a polyurethane resin in view of applying performance, resin characteristic, applicator adaptability and productivity.

Illustrative example of the polyurethane resin includes a resin composed of a polyisocyanate and a polyol. Illustrative example of the polyisocyanate includes: a diisocyanate compound such as a tolylene diisocyanate, a diphenylmethane diisocyanate, a polymethylene polyphenyl diisocyanate, a hexamethylene diisocyanate and a xylylene diisocyanate; a diisocyanate compound derived from a diol or a diamine and a diisocyanate; a triisocyanate produced from a one-molecule trimethylolpropane and a three-molecule toluylene diisocyanate and a derivative thereof; and a blocked isocyanate obtained by masking the isocyanate group with a blocking agent such as a phenol and a cresol.

Illustrative example of the polyol includes a compound having two or more hydroxyl groups in one molecule such as an ethylene glycol, a polyethylene glycol, a propylene glycol and a polypropylene glycol.

These resins are used as a solution when synthetic fibers bundled are glued.

Preferred illustrative example of the solvent used as a solution includes the one with easy recovery and recycling and high evaporation rate, specifically, a methylene chloride, a methanol, an acetone and an ethyl acetate in particular and a phenol, a cresol, a dimethylformamide and a dimethylacetamide combined.

As to the resin solution, the resin concentration is preferably 4 to 30% by weight, depending on impregnation conditions, more preferably 2 to 30% by mass, particularly preferably 2 to 20% by mass, and much more preferably the viscosity is 50 cps or less.

In the applicator of the present invention, it is preferable to obtain the columnar brush member 30 by gluing synthetic fibers bundled by using the resin.

The hardness of an outer periphery of the columnar brush member 30 can be made higher than the hardness of the central portion. This means that the outer periphery can be made harder and the central portion can be made softer by containing a resin at the outer periphery in large quantities (instead, less at the central portion).

Specifically, this step is performed by controlling the amount of a solvent removed from a resin solution impregnated in the synthetic fibers bundled.

Illustrative example of the means for gluing synthetic fibers bundled by containing a resin at the outer periphery in large quantities includes a method for infiltrating synthetic fibers bundled cut into an appropriate length in a resin solution for a certain period of time or spraying synthetic fibers bundled with the resin solution.

The synthetic fibers bundled can contain a resin at the outer periphery in large quantities by changing the resin concentration of the resin solution.

Another embodiment of forming the columnar brush member body 31 and the columnar brush member neck portion 32 is to apply a thermoplastic resin having a lower softening point than the temperature of a mold heated inside the mold heated at a higher temperature than a softening point of synthetic fibers used and press the synthetic fibers bundled composed of fine polyester fibers with the mold.

By attaching a synthetic resin film to a portion corresponding to the columnar brush member body 31 and the columnar brush member neck portion 32, the columnar brush member body 31 and the columnar brush member neck portion 32 can be formed.

By supplying the synthetic fibers into a mold heated at a higher temperature than the melting point of synthetic fibers used, the synthetic fibers at a portion of synthetic fibers composed of polyester fibers heated coming into contact with the mold are fused.

Consequently, only an outer surface portion of synthetic fibers bundled composed of fine polyester fibers can be solidified to integrate the columnar brush member body 31.

Next, by grinding the entire outer periphery of an end portion of the synthetic fibers bundled solidified with an adhesive which is contained on the outer periphery in large quantities, a tip portion of the synthetic fibers bundled can readily be unraveled.

The columnar brush member tip portion 33 of the columnar brush member 30 used in Example 1 has a fan shape.

Herein, the fan shape extends in a perpendicular lateral direction against a pillar axial lengthwise direction.

Specifically, the maximum width of the columnar brush member tip portion 33 is larger than the maximum size of the columnar brush member body 31, and a thickness of a tip 34 of the columnar brush member tip portion 33 is smaller than the maximum size of the columnar brush member body 31, with a cross section by a plane horizontal to the pillar axial lengthwise direction of the columnar brush member 30 as a standard.

Herein, a thickness of the tip 34 of the columnar brush member tip portion 33 is determined, with the length of a perpendicular lengthwise direction against the pillar axial lengthwise direction as a standard.

The perpendicular lateral direction and the perpendicular lengthwise direction mean directions orthogonal to each other on a plane perpendicular to the pillar axial lengthwise direction.

The maximum width of the fan-shaped columnar brush member tip portion 33 of the columnar brush member 30 is preferably 1.1 to 2.0 times the maximum size of the columnar brush member body 31, with a cross section by a plane horizontal to the pillar axial lengthwise direction of the columnar brush member 30 as a standard.

When the shape of the fan-shaped columnar brush member tip portion 33 is within the above range, the applicator according to Example 1 can readily be handled.

The columnar brush member 30 is formed so that a thickness of the fan-shaped columnar brush member tip portion 33 of the columnar brush member 30 decreases toward the tip 34 of the columnar brush member 30.

In order to make a smaller thickness of the fan-shaped columnar brush member tip portion 33 toward the tip 34 of the columnar brush member 30, the columnar brush member neck portion 32 is formed at one end of the columnar brush member body 31 by commonly known processing means such as cutting tool and grinding stone. Subsequently, the columnar brush member neck portion 32 is ground so as to make a thickness smaller toward the tip. Thereafter, synthetic fibers bundled fixed with an adhesive of the tip portion are unraveled by a secondary processing to tear apart the fibers into a brush shape and form the shape into a fan.

By changing the shape after grinding process or the extent of unraveling in the secondary processing, the fan-shaped width of the columnar brush member neck portion can be changed in an intended manner.

Since the fan-shaped columnar brush member tip portion 33 is unraveled, part or all of synthetic fibers of the tip portion of the synthetic fibers bundled can freely move by the contact stress with an affected part in use.

As illustrated in the schematic perspective view in FIG. 5, the tip 34 of the columnar brush member 30 used in Example 1 has a surface having a belt-like predetermined area.

A dashed line a-a shown in the schematic plan view in FIG. 6 represents a central line of the tip 34 of the columnar brush member 30.

Figure 7:
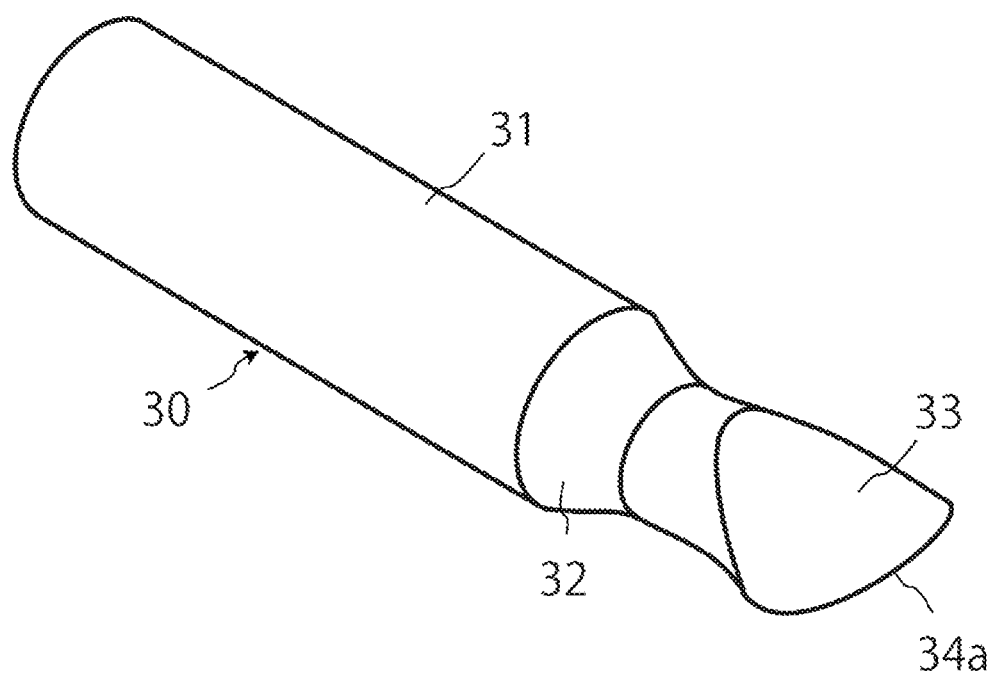
FIG. 7 is a schematic perspective view illustrating another embodiment of a columnar brush member.

FIG. 7 is a schematic perspective view illustrating another embodiment of the columnar brush member 30 illustrated in FIG. 5.

As illustrated in FIG. 7, the tip 34 of the columnar brush member 30 may be linear. In this case, a tip 34 of the columnar brush member 30 shown in FIG. 7 is linearly formed at the position of the central line of the tip 34 of the columnar brush member 30 indicated by the dashed line a-a of the schematic plan view in FIG. 6.

In Example 1, the fan-shaped columnar brush member tip portion 33 of the columnar brush member 30 is symmetrically formed, with a dashed line a-a shown in FIG. 6 as a standard, so that a thickness of the fan-shaped columnar brush member tip portion 33 decreases toward the tip 34 of the columnar brush member 30. In addition, a shape formed by cutting the columnar brush member tip portion 33 of the columnar brush member 30 in one direction from one side to the other side can be adopted accordingly.

Polyester synthetic fibers are used in Example 1 as synthetic fibers used for the columnar brush member 30. Also, synthetic fibers such as nylon fibers and acrylic fibers can be used together with or instead of the polyester fibers.

The synthetic fibers can be used alone or in combination with one or more types thereof.

Synthetic fibers used in the present invention are preferably 7 to 50 µm in diameter, and more preferably 10 to 30 µm. Since the fan-shaped columnar brush member tip portion 33 of the columnar brush member 30 obtained is soft within the range of fiber diameter, irritation on an affected part of a patient and pain can be reduced, even when the columnar brush member tip portion 33 contacts with the affected part of a patient.

When the fiber diameter is under 7 µm, the tip portion of the columnar brush member is soft but ultrafine, thereby making it difficult to produce the columnar brush member and leading to cost increase.

When the fiber diameter is more than 50 µm, the tip portion of the columnar brush member is too hard, which is like to irritate an affected part.

The density of synthetic fibers used in the present invention and an adhesive gluing the same is preferably 0.15 to 0.65 (porosity: 85% to 35%), and more preferably 0.25 to 0.50 (porosity: 75% to 50%).

Since a structure portion is small when the density of the synthetic fibers is less than 0.15, it is difficult to maintain the strength of the columnar brush member body. In addition, it is hard to maintain the shape and easy to break down.

When a drug flow path (gap) becomes smaller with the density of the synthetic fibers exceeding 0.65, it is hard for a drug to be supplied, resulting in difficulty in smooth drug application. In particular, the amount of a drug to be applied is likely to be small. As the tip portion of the columnar brush member hardens, an affected part can readily be irritated.

By inserting the columnar brush member 30 into the opening 14 of the solution container 10, the applicator 100 according to Example 1 can be obtained.

As shown in FIG. 2 described above, the protruding portion 17 for supporting the columnar brush member 30 is provided on an inner surface of the solution container neck portion 12 of the solution container 10.

The protruding portion 17 has an annular shape, and is disposed along an inner surface of the solution container neck portion 12. By providing the protruding portion 17, it is possible to prevent the columnar brush member 30 from falling down inside the solution container 10 when the columnar brush member 30 is inserted into the opening 14 of the solution container 10.

A solution can be contained inside the solution container 10. It is preferable that the solution used in the present invention be a tinea unguium medicine.

When the applicator 100 according to Example 1 is retained with the columnar brush member 30 facing downward, the solution placed inside the solution container 10 reaches an end face of the columnar brush member 30.

When the solution reaches the end face of the columnar brush member 30, it reaches the tip portion 33 opposite to an end face of the columnar brush member 30 by capillarity of the columnar brush member 30. Accordingly, the solution can be applied to an affected part by using the applicator 100 according to Example 1.

Since an outer surface of the columnar brush member 30 is firmly attached to an inner surface of the opening 14 of the solution container 10, there is no gap between the outer surface of the columnar brush member 30 and the inner surface of the opening 14 of the solution container 10.

Consequently, it is possible to prevent a solution inside the solution container 10 from leaking from a gap between the outer surface of the columnar brush member 30 and the inner surface of the opening 14 of the solution container 10.

Next, the applicator 100 according to Example 1 may comprise a lid member.

Figure 8:
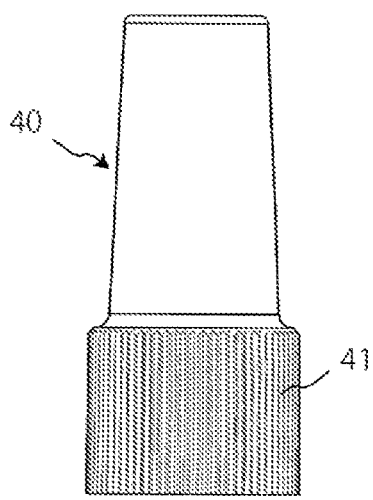
FIG. 8 is a schematic front view for describing a lid member used in Example 1.
Figure 9:
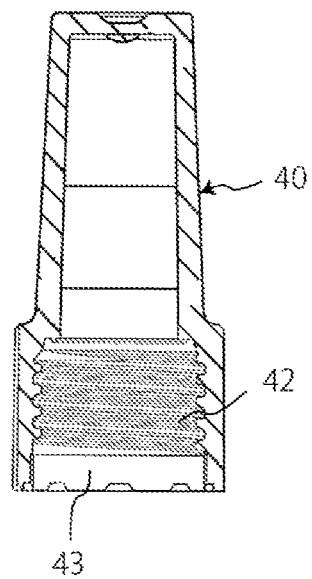
FIG. 9 is a schematic sectional view illustrating a lid member used in Example 1.
Figure 10:
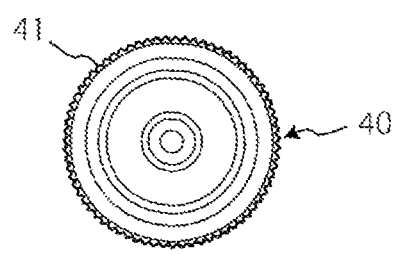
FIG. 10 is a schematic plan view illustrating a lid member viewed from above.
Figure 11:
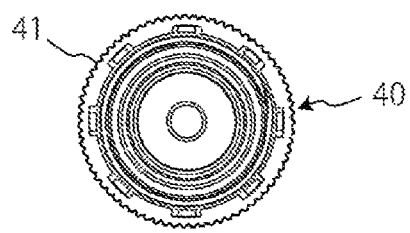
FIG. 11 is a schematic bottom view illustrating a lid member viewed from below.

FIG. 8 is a schematic front view for describing a lid member used in Example 1, FIG. 9 is a schematic sectional view illustrating a lid member used in Example 1, FIG. 10 is a schematic plan view illustrating a lid member shown in FIG. 8 viewed from above, and FIG. 11 is a schematic bottom view illustrating a lid member shown in FIG. 8 viewed from below.

The lid member 40 is a lidded cylindrical shape having an opening 43 at one end. Pluralities of linear grooves 41 are provided parallel to each other in a lengthwise direction on an outer surface of the lid member 40, so that the lid member 40 causes no slip when it is rotated by using fingers.

A thread groove 42 is provided inside the lid member 40. By combining the thread groove 42 inside the lid member 40 and the screw thread 15 provided on an outer surface of the solution container neck portion 12 of the solution container 10 described above in FIG. 1 to be rotated in direction opposite to each other, the lid member 40 and the solution container 10 are sealed to each other to be fixed.

Consequently, it is possible to prevent a solution retained by being placed inside the solution container 10 from evaporating and drying.

While the Example 1 describes that the lid member 40 and the solution container 10 are sealed and fixed via a screw structure, means for fixing the lid member 40 and the solution container 10 used in the present invention is not restricted, but any means can be accordingly selected and used if it can seal and fix the same.

Figure 12:
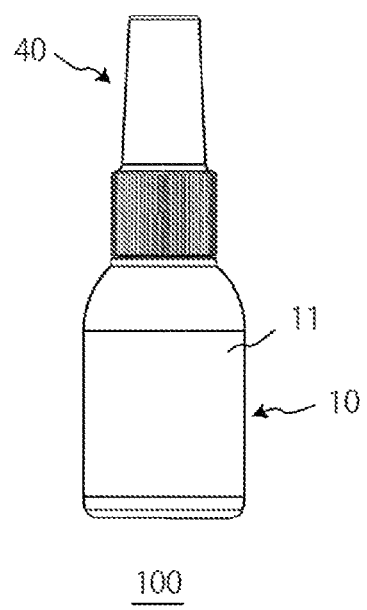
FIG. 12 is a schematic front view illustrating a whole picture of the applicator according to Example 1.
Figure 13:
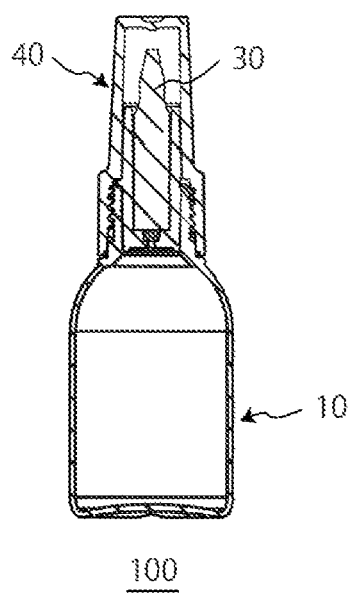
FIG. 13 is a schematic sectional view illustrating the applicator according to Example 1.
Figure 14:
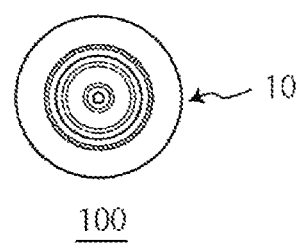
FIG. 14 is a schematic plan view illustrating the applicator according to Example 1 viewed from above.

FIG. 12 is a schematic front view illustrating a whole picture of the applicator 100 according to Example 1, FIG. 13 is a schematic sectional view illustrating the applicator 100 according to Example 1, and FIG. 14 is a schematic plan view illustrating the applicator 100 according to Example 1 shown in FIG. 12 viewed from above.

As shown in FIG. 12, the lid member 40 and the solution container 10 can be sealed and fixed to each other.

As shown in FIG. 13, the columnar brush member 30 is contained inside the lid member 40.

As illustrated in FIGS. 12 to 14, the applicator 100 in Example 1 can seal and preserve a solution inside the same. Since its shape is excellent in portability, a patient can accordingly apply a solution to an affected part by himself in daily life.

Example 2

An applicator 110 according to Example 2 comprises at least a solution container, a bottomed tubular holder and a columnar brush member. The solution container used in Example 2 will be firstly described.

Figure 15:
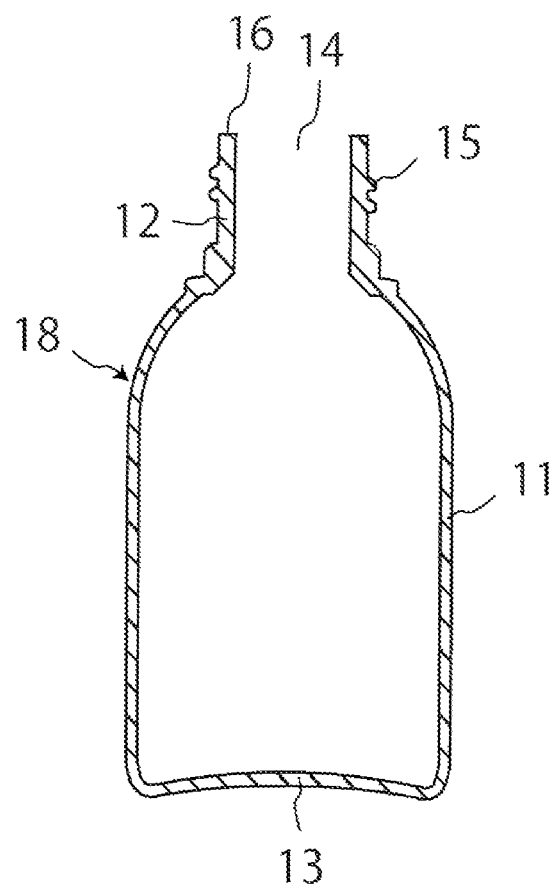
FIG. 15 is a schematic sectional view of a solution container 18 used in Example 2.
Figure 16:
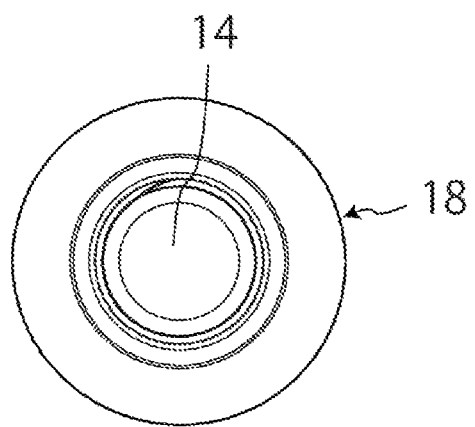
FIG. 16 is a schematic plan view illustrating a solution container used in Example 2 from above.

FIG. 15 is a schematic sectional view illustrating a solution container 18 used in Example 2, and FIG. 16 is a schematic plan view illustrating a solution container 18 used in Example 2 viewed from above.

In Example 2, a solution container 18 is used instead [[f]] of the solution container 10 used in Example 1.

In the solution container 18 used in Example 2, a protruding portion 17 disposed on the inner surface of the solution container neck portion 12 of the solution container 10 used in Example 1 is not described. The other descriptions of the solution container 18 apply to the solution container 10 used in Example 1.

The applicator 110 according to Example 2 is different from the applicator 100 according to Example 1 in that a bottomed tubular holder 20 is disposed between the solution container 18 and the columnar brush member 30.

Figure 17:
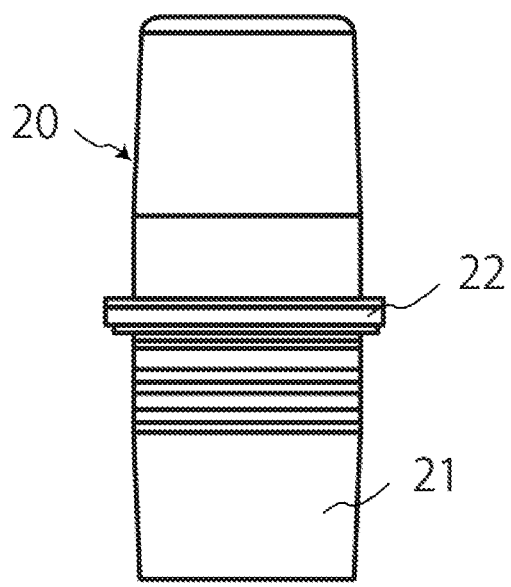
FIG. 17 is a schematic front view for describing a bottomed tubular holder used in Example 2.
Figure 18:
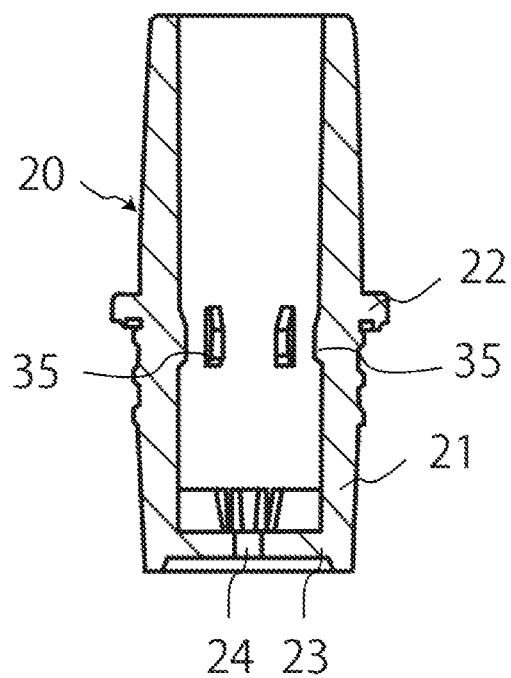
FIG. 18 is a schematic sectional view of a bottomed tubular holder.
Figure 19:
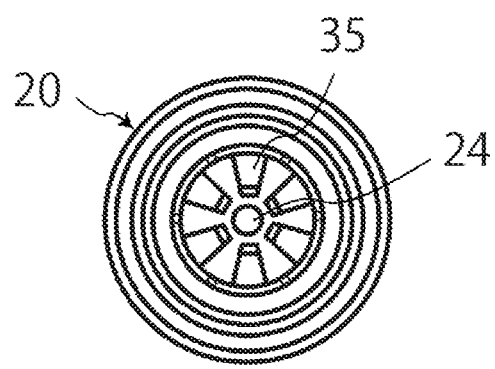
FIG. 19 is a schematic plan view illustrating a bottomed tubular holder viewed from above.
Figure 20:
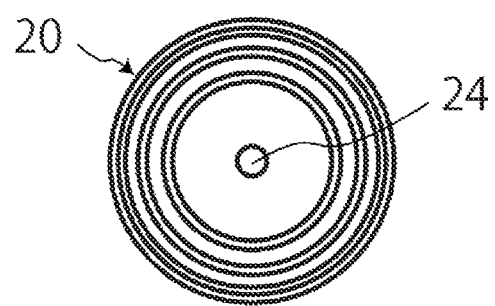
FIG. 20 is a schematic bottom view illustrating a bottomed tubular holder viewed from below.

FIG. 17 is a schematic front view for describing a bottomed tubular holder used in Example 2, FIG. 18 is a schematic sectional view of a bottomed tubular holder illustrated in FIG. 17, FIG. 19 is a schematic plan view of a bottomed tubular holder illustrated in FIG. 17 viewed from above, and FIG. 20 is a schematic bottom view of a bottomed tubular holder illustrated in FIG. 17 viewed from below.

The bottomed tubular holder 20 used in Example 2 comprises a bottomed tubular holder body 21 and an annular flange 22. The bottomed tubular holder body 21 has a tubular shape. The tubular shape can be changed according to a peripheral shape of the columnar brush member 30 so that the columnar brush member 30 used in Example 1 can be inserted thereinto.

The material of the bottomed tubular holder 20 used in Example 2 is the same as the solution container 10 used in Example 1.

As illustrated in the schematic sectional view in FIG. 18, the bottomed tubular holder 20 has a bottom portion 23, and the bottom portion 23 and the tubular bottomed tubular holder body 21 are bonded with each other with no gap.

The center of the bottom portion 23 is provided with a pore 24. A solution placed in the solution container 10 via the pore 24 can move inside the bottomed tubular holder 20.

The location, number, shape and size of the pore 24 can be determined according to properties such as the viscosity of a solution used.

The pore 24 used in Example 2 has a circular shape, but the shape of the pore 24 is not restricted thereto. Other shapes such as ellipse, polygon and parallelogram can be selected according to the purpose or use.

The maximum size of the pore 24 is preferably 0.5 to 5 mm, with a plane parallel to the bottom portion 23 as a standard.

This range is preferable because the solution can smoothly move and the solution doesn't fall from the columnar brush member. The maximum size is preferably 0.5 to 2 mm and more preferably 0.8 to 1.2 mm.

Meanwhile, an outer surface of the bottomed tubular holder body 21 is provided with an annular flange 22, so that the annular flange 22 externally protrudes. The shape of the bottom face of the annular flange 22 approximately corresponds to the shape of the end face 16 of the opening 14 of the solution container 18 above described, and it is possible to prevent the bottomed tubular holder 20 from falling inside the solution container 18 when the bottomed tubular holder 20 is inserted into the inside of the solution container 18.

Also, it is possible to prevent a solution from leaking from a gap between the bottomed tubular holder 20 and the solution container 18, because the bottom face of the annular flange 22 and the end face 16 of the opening 14 of the solution container 18 come in contact with each other with no gap when the bottomed tubular holder 20 is inserted into the solution container 18.

The largest portion of the outer surface of the bottomed tubular holder body 21 has a shape which is almost the same as the inner surface of the solution container neck portion 12 of the solution container 18. Therefore, the bottomed tubular holder 20 can be disposed on an inner surface of the drug container neck portion 22 with no gap.

In addition, the inner surface of the bottomed tubular holder body 21 is symmetrically provided with supporting members 35 for supporting a columnar brush member with regular intervals, with the pore 24 as a center.

By providing the supporting members 35, a later-described columnar brush member can be fixed to the bottomed tubular holder body 21 when the columnar brush member is inserted into the inside of the bottomed tubular holder body 21.

A space can be provided between the end face of the columnar brush member 30 and the bottom portion 23 of the bottomed tubular holder body 21.

By providing the space, a solution is not taken up by capillarity of the columnar brush member 30 when the columnar brush member 30 is faced upward to allow an applicator 110 to stand on a plane such as a desk, and it is possible to delay evaporation of the solution inside the solution container 18.

A structure for providing a space between the end face of the columnar brush member 30 and the bottom portion 23 of the bottomed tubular holder body 21 is not restricted. However, by disposing a protruding portion at the bottom portion 23, it is possible to prevent the end face of the columnar brush member 30 from directly contacting with the bottom portion 23 of the bottomed tubular holder body 21 to provide the space.

Like in Example 1, the applicator 110 according to Example 2 can contain a solution inside the solution container 18.

The solution is preferably a tinea unguium medicine.

Next, like in Example 1, the applicator 110 according to Example 2 may comprise a lid member.

The lid member 40 used in Example 2 is the same as the lid member 40 used in Example 1.

Like in Example 1, means for fixing the lid member 40 and the solution container 18 used in Example 2 is not restricted, and any means can be selected and used accordingly if it can seal and fix the same.

Figure 21:
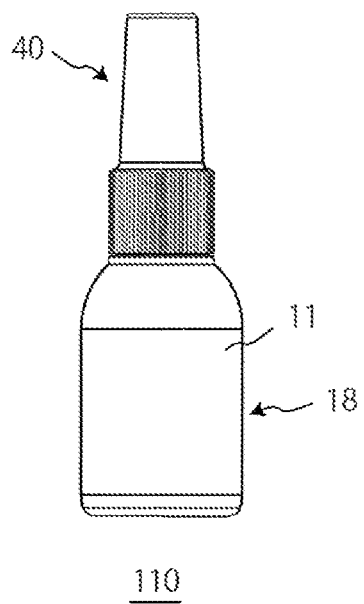
FIG. 21 is a schematic front view illustrating a whole picture of the applicator according to Example 2.
Figure 22:
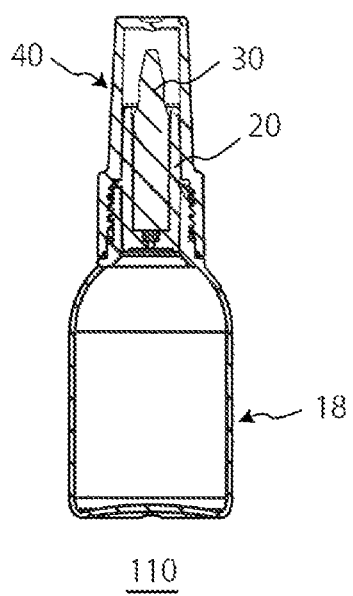
FIG. 22 is a schematic sectional view illustrating the applicator according to Example 2.
Figure 23:
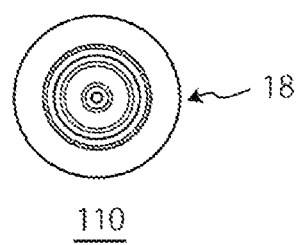
FIG. 23 is a schematic plan view illustrating the applicator according to Example 2 viewed from above.

FIG. 21 is a schematic front view illustrating a whole picture of the applicator 110 according to Example 2, FIG. 22 is a schematic sectional view illustrating the applicator 100 according to Example 2, and FIG. 23 is a schematic plan view illustrating the applicator 110 according to Example 2 shown in FIG. 21 viewed from above.

As shown in FIG. 21, the lid member 40 and the solution container 18 can be sealed and fixed to each other.

As shown in FIG. 22, the columnar brush member 30 is contained inside the lid member 40.

As illustrated in FIGS. 21 to 23, the applicator 110 of Example 2 can also seal and preserve a solution inside the same. A patient can apply a solution by himself to an affected part in daily life due to a shape having excellent portability.

When the applicator 110 according to Example 2 is retained with the columnar brush member 30 facing downward, a solution placed inside the solution container 18 comes inside the bottomed tubular holder 20 via the pore 24 provided at the bottom portion 23 of the bottomed tubular holder 20 to reach the end face of the columnar brush member 30.

By the pore 24 provided at the bottom portion 23 of the bottomed tubular holder 20, the amount of a solution that moves from the solution container 18 to the bottomed tubular holder 20 is controlled. Accordingly, it is possible to control the movement of a large volume of a solution to the columnar brush member 30 at one time, even when the solution container 18 is tilted to the opening 14 thereof or faced downward.

A solution that have reached the end face of the columnar brush member 30 reaches the tip portion 33 opposite to the end face of the columnar brush member 30 by capillarity thereof. Accordingly, a solution can be applied to an affected part by using the applicator 110 according to Example 2.

The columnar brush member 30 formed by bundling synthetic fibers in a columnar shape is inserted into the inside of the bottomed tubular holder 20.

The inner surface of the bottomed tubular holder 20 and the outer surface of the columnar brush member 30 are firmly attached with each other having no gap. Therefore, it is possible to prevent a liquid from leaking from a gap between the inner surface of the bottomed tubular holder 20 and the outer surface of the columnar brush member 30.

Consequently, a solution is provided at the columnar brush member 30 of the applicator 110 according to Example 2, and it is possible to prevent a solution from leaking from the tip of the columnar brush member 30.

A conventional drug applicator can readily cause liquid dripping or evaporation of a solution from a drug container. Conversely, in the applicator 110 according to Example 2, columnar brush members 30 formed by bundling synthetic fibers in a columnar shape are inserted into the inside of the bottomed tubular holder 20 with no gap.

Accordingly, no liquid dripping is found by a solution inside the applicator 110, even when the columnar brush member 30 of the applicator 110 according to Example 2 is faced downward, and a solution can thinly be applied to an affected part by using the columnar brush member 30.

By using the applicator 110 according to Example 2 in this manner, there is no leakage of the solution from between the nail and the skin, even when a solution such as a tinea unguium medicine is applied therebetween. Therefore, the solution can readily be applied to an affected part.

In addition, the applicator 110 according to Example 2 can rarely cause dropping of solution, thereby making it difficult to apply a solution such as a tinea unguium medicine as an eyewash, by taking the applicator 110 for a container for applying an eyewash.

Consequently, it is possible to prevent an accidental injury from misuse of a solution.

Additionally, the applicator 110 has no hole for visually confirming that leads externally from the solution container 18, and evaporation of a solution inside the solution container 18 can be reduced.

Also, by providing supporting members 35 inside the bottomed tubular holder 20, a space can also be provided between the bottom portion 23 of the bottomed tubular holder 20 and the end face of the columnar brush member 30. When the bottomed tubular holder 20 is allowed to stand with the columnar brush member 30 facing upward, it is possible to prevent a solution inside the bottomed tubular holder 20 from directly contacting with the columnar brush member 30 by providing the space.

Consequently, evaporation of the solution can be reduced in comparison with a conventional drug applicator.

In case of a conventional drug applicator, the internal pressure of the drug applicator can be increased due to outside air temperature. When a drug is sprayed from the conventional drug applicator to an affected part with a high internal pressure, irritation on the affected part grows.

On the contrary, since the applicator 110 according to Example 2 is less influenced by outside air temperature, liquid dripping is rarely found even with a higher outside air temperature. Consequently, it is possible to keep irritation on an affected part smaller, even when outside air temperature changes.

[Performance Evaluation of Applicator 110 According to Example 2]

The applicator 110 according to Example 2 was used to perform a 3-month test on the condition of a low relative humidity (40° C.±2° C./25% RH or less), in accordance with an item [2.2.7.3. Drug Product Packed in Semi-permeable Container] stated in the Notification from the Director of Evaluation and Licensing Division, Pharmaceutical and Food Safety Bureau, the Ministry of Health, Labour and Welfare [Stability Testing Guideline for New Drug Substances and Products Containing Active Ingredients (No. 0603001)] as of Jun. 3, 2003 to evaluate an impact of difference in the amount of a solution filled on mass decrease from the applicator 110 according to the present invention and liquid leakage.

(1) Description of the Test

The amount of a solution filled in the applicator 110 according to Example 2 was changed and filled in the solution container 18. After the columnar brush member 30 and the bottomed tubular holder 20 were attached, a specimen was prepared by sealing the solution container 18 with the lid member 40 with a pressure of approx. 60N·cm by using a torque meter.

Next, the transpiration rate (%) of the specimen preserved for a certain period of time (upon test, 7, 14, 21, and 28 days and 2 and 3 months after the test) on the condition of 40° C.±2° C./25% RH or less was measured with the specimen each overturned, and the mass decrease was confirmed. The amount to be filled was 3, 5 and 8 mL.

(2) Test Material and Test Method (2-1) Test Material 2-1-1) Solution

60% An alcohol solution was used as a specimen.

2-1-2) Applicator 110

Solution container 18: HDPE (high-density polyethylene, weight: 2.6 g)

Bottomed tubular holder 20: PP (polypropylene)

Lid member 40: PP (polypropylene)

Columnar brush member 30: polyester (3) Test Method (3-1) Preparation of Specimen After filling 3, 5 and 8 mL of a solution into the solution container 18, the columnar brush member 30 and the bottomed tubular holder 20 were attached thereto, and a specimen was prepared by sealing the solution container 18 with the lid member 40 with a pressure of approx. 60N·cm by using a torque meter.

(4) Description of the Test

[Impact of Difference in the Amount of Filling on Mass Decrease]

As to the specimen prepared in the (3-1), the mass per specimen was precisely measured according to the following preservation conditions and measurement periods to calculate the transpiration rate (%), and the mass decrease was confirmed. Herein, the transpiration rate was calculated by using the following formula.

Transpiration rate (%) =

[(Mass of applicator 110 before test of filling solution –

Mass of applicator 110 after test of filling solution)/

-continued $$[\text{Mass of applicator 110 before test of filling solution} - \text{Mass of applicator 110 before test of not filling solution}] \times 100$$

[Confirmation of Liquid Leakage]

As to the specimen, liquid leakage was visually confirmed according to the following preservation conditions and measurement periods.

(Preservation Conditions)

40° C.±2° C./25% RH or less

Preserved with overturned (Measurement Period)

upon test, 7, 14, 21 and 28 days and 2 and 3 months after the test (5) Results of the Test (5-1) Impact of Difference in the Amount of Filling on Mass Decrease In all the containers, it was found that the rate of mass decrease per amount filled grew by decrease in the amount filled. An obvious change in quality stated in the Stability Testing Guideline (5% moisture loss) was not found.

(5-2) Confirmation of Liquid Leakage

Liquid leakage was not confirmed with the state of being overturned.

Table 1 shows the results.

TABLE 1

|  | the 7th day | the 14th day | the 21st day | the 28th day | the 2nd month | the 3rd month |
|---|---|---|---|---|---|---|
| 3 mL transpiration rate | 0.28 | 0.58 | 0.91 | 1.25 | 2.85 | 4.31 |
| liquid leakage | none | none | none | none | none | none |
| 5 mL transpiration rate | 0.17 | 0.36 | 0.56 | 0.75 | 1.73 | 2.62 |
| liquid leakage | none | none | none | none | none | none |
| 8 mL transpiration rate | 0.10 | 0.22 | 0.35 | 0.47 | 1.08 | 1.64 |
| liquid leakage | none | none | none | none | none | none |

* The transpiration rate is displayed at a percentage.

As shown in Table 1, the applicator according to the present invention causes no liquid leakage, even when the applicator contains a volatile solution containing an alcohol such as ethanol and propanol by 50% by weight or more. When liquid leakage is found from an applicator, a cloth pocket or a bag containing the applicator is prone to odor and stain of a drug, but the applicator according to the present invention is free from such problems and excellent in daily portability as well.

INDUSTRIAL APPLICABILITY

The applicator of the present invention can readily be used due to less dripping of a solution. Also, it is hard for a solution therein to evaporate. In addition, with less irritation on an affected part of a patient having tinea unguium symptoms, the applicator of the present invention can widely be used as a container for applying a drug for treating tinea unguium in particular.

EXPLANATION OF REFERENCES

10,18 Solution container
11 Solution container body
12 Solution container neck portion
13,23 Bottom portion
14,43 Opening
16 End surface
17 Protruding portion
20 Bottomed tubular holder
21 Bottomed tubular holder body
22 Annular flange
24 Pore
25 Screw thread
35 Supporting member
30 Columnar brush member
31 Columnar brush member body
32 Columnar brush member neck portion
33 Columnar brush member tip portion
34 Tip
40 Lid member
41 Linear groove
42 Thread groove
100 Applicator according to Example 1
110 Applicator according to Example 2
Dashed line a-a Central line of tip columnar brush member

The invention claimed is:

1. An applicator, comprising a solution container having a neck portion, which is provided with a circular opening, and a columnar brush member obtained by impregnating a bundle of synthetic fibers with an adhesive and then grinding the bundle of synthetic fibers, wherein
the columnar brush member is disposed at the opening of the solution container, and
a tip portion of the columnar brush member is a brush and is disposed outside the solution container, and an end face of the columnar brush member is put in the solution container,
a tip portion of the columnar brush member has a fan shape extending in a perpendicular lateral direction against a vertical longitudinal direction, and
a thickness of the fan-shaped tip portion of the columnar brush member decreases in a perpendicular lengthwise direction against the vertical longitudinal direction toward the tip portion of the columnar brush member, wherein
the perpendicular lateral direction and the perpendicular lengthwise direction are directions orthogonal to each other on a plane perpendicular to the vertical longitudinal direction, and
a capillary is formed as a gap for supplying a solution between the synthetic fibers inside the columnar brush member from an end face of the columnar brush member to the tip portion opposite to the end face of the columnar brush member by capillarity thereof,
wherein the columnar brush member is formed by bundling synthetic fibers 7 to 50 μm in diameter so that the density ranges from 0.15 to 0.65, wherein the density is the rate of synthetic fibers per sectional area to an adhesive gluing the same, with a cross section cut perpendicular to the vertical longitudinal direction of the columnar brush member,
a bottomed tubular holder having a tubular body and a bottom portion is provided between the solution container and the columnar brush member,
the bottomed tubular holder comprises a supporting member inside said holder, the bottomed tubular holder is inserted into the opening of the solution container,
the bottom portion of the bottomed tubular holder has at least one pore and the solution enters the bottomed tubular holder via said at least one pore, and
the columnar brush member is inserted inside of the tubular body of the bottomed tubular holder, wherein the applicator is retained with the columnar brush member facing downward, and a solution placed inside the solution container enters the bottomed tubular holder via the at least one pore provided at the bottom portion of the bottomed tubular holder to reach an end face of the columnar brush member, and the solution in the solution container is an athlete's foot medicine or a liquid tinea unguium medicine.

2. The applicator according to claim 1, wherein a maximum width of the fan-shaped tip portion of the columnar brush member is 1.1 to 2.0 times a maximum size of a columnar portion of the columnar brush member, with a cross section by a plane horizontal to the vertical longitudinal direction of the columnar brush member as a standard.

3. The applicator according to claim 1, wherein
synthetic fibers used for the columnar brush member are at least one selected from the group consisting of polyester fibers, nylon fibers and acrylic fibers.

4. The applicator according to claim 3, wherein
the adhesive is contained on the outer periphery of the synthetic fibers bundled in large quantities,
a tip portion of the synthetic fibers bundled is ground to be unraveled over the entire outer periphery of at least one end of the synthetic fibers bundled, and
synthetic fibers of part or all of the tip portion of the synthetic fibers bundled move by contact stress in use.

5. The applicator according to claim 4, wherein the applicator comprises a lid member, wherein the lid member is sealed and fixed to the solution container.

6. The applicator according to claim 5, wherein a volatile solution is contained in the solution container.

7. The applicator according to claim 1, wherein
the supporting member supports the columnar brush member inserted into the inside of the tubular body of the bottomed tubular holder, and
a space is provided between an end face of the columnar brush member closely inserted into the inside of the bottomed tubular holder and the bottom portion of the bottomed tubular holder.

8. A method of treating tinea unguium by using an applicator for applying a solution for treating tinea unguium to an affected part of a patient, wherein
the applicator comprises a solution container having an opening, a bottomed tubular holder, and a columnar brush member comprising synthetic fibers,
the bottomed tubular holder having a tubular body and a bottom portion is provided between the solution container and the columnar brush member,
the bottom portion of the bottomed tubular holder has at least one pore and the solution enters the bottomed tubular holder via said at least one pore,
the amount of a solution that moves from the solution container to the bottomed tubular holder is controlled by the at least one pore provided at the bottom portion of the bottomed tubular holder, and
the columnar brush member is inserted inside of the tubular body of the bottomed tubular holder, wherein
the applicator is retained with the columnar brush member facing downward, and a solution placed inside the solution container enters the bottomed tubular holder via the at least one pore provided at the bottom portion of the bottomed tubular holder to reach an end face of the columnar brush member, and
a capillary is formed as a gap for supplying the solution between the synthetic fibers inside the columnar brush member from an end face of the columnar brush member to the tip portion opposite to the end face of the columnar brush member by capillarity thereof.

9. The method according to claim 8, wherein
the columnar brush member formed by bundling of the synthetic fibers in a columnar shape is inserted into the inside of the bottomed tubular holder, wherein
a tip portion of the columnar brush member outside the solution container has a fan shape extending in a perpendicular lateral direction against a vertical longitudinal direction, and a thickness of the fan-shaped tip portion of the columnar brush member decreases in a perpendicular lengthwise direction against the vertical longitudinal direction toward the tip portion of the columnar brush member, wherein the perpendicular lateral direction and the perpendicular lengthwise direction are directions orthogonal to each other on a plane perpendicular to the vertical longitudinal direction.

10. A method of treating tinea unguium by using an applicator for applying a solution for treating tinea unguium to an affected part of a patient, wherein
the applicator comprises a solution container having a neck portion, which is provided with a circular opening, and a columnar brush member obtained by impregnating a bundle of synthetic fibers with an adhesive and then grinding the bundle of synthetic fibers, wherein
the columnar brush member is disposed at the opening of the solution container, and
a tip portion of the columnar brush member outside the solution container is a brush and has a fan shape extending in a perpendicular lateral direction against a vertical longitudinal direction, and a thickness of the fan-shaped tip portion of the columnar brush member decreases in a perpendicular lengthwise direction against the vertical longitudinal direction toward the tip portion of the columnar brush member, wherein
the perpendicular lateral direction and the perpendicular lengthwise direction are directions orthogonal to each other on a plane perpendicular to the vertical longitudinal direction, and a capillary is formed as a gap for supplying a solution between the synthetic fibers inside the columnar brush member from that has reached end face of the columnar brush member reaches to the tip portion opposite to the end face of the columnar brush member by capillarity thereof,
wherein the columnar brush member is formed by bundling synthetic fibers 7 to 50 μmin diameter so that the density ranges from 0.15 to 0.65, wherein the density is the rate of synthetic fibers per sectional area to an adhesive gluing the same, with a cross section cut perpendicular to the vertical longitudinal direction of the columnar brush member,
a bottomed tubular holder having a tubular body and a bottom portion is provided between the solution container and the columnar brush member,
the bottomed tubular holder comprises a supporting member inside said holder, the bottomed tubular holder is inserted into the opening of the solution container,
the bottom portion of the bottomed tubular holder has at least one pore and the solution enters the bottomed tubular holder via said at least one pore, and
the columnar brush member is inserted inside of the tubular body of the bottomed tubular holder, wherein
the applicator is retained with the columnar brush member facing downward, and a solution placed inside the solution container enters the bottomed tubular holder via the at least one pore provided at the bottom portion of the bottomed tubular holder to reach an end face of the columnar brush member.

11. The method according to claim 10, wherein a maximum width of the fan-shaped tip portion of the columnar brush member is 1.1 to 2.0 times a maximum size of a columnar portion of the columnar brush member, with a cross section by a plane horizontal to the vertical longitudinal direction of the columnar brush member as a standard.

12. The method according to claim 10, wherein
synthetic fibers used for the columnar brush member are at least one selected from the group consisting of polyester fibers, nylon fibers and acrylic fibers.

13. The method according to claim 12, wherein
the adhesive is contained on the outer periphery of the synthetic fibers bundled in large quantities,
a tip portion of the synthetic fibers bundled is ground to be unraveled over the entire outer periphery of at least one end of the synthetic fibers bundled, and
synthetic fibers of part or all of the tip portion of the synthetic fibers bundled move by contact stress in use.

14. The method according to claim 12, wherein
the applicator comprises a lid member, wherein the lid member is sealed and fixed to the solution container.

15. The method according to claim 14, wherein
a volatile solution is contained in the solution container.

16. The method according to claim 10, wherein
the supporting member supports the columnar brush member inserted into the inside of the tubular body of the bottomed tubular holder, and
a space is provided between an end face of the columnar brush member closely inserted into the inside of the bottomed tubular holder and the bottom portion of the bottomed tubular holder.

* * * * *